United States Patent [19]

Beyler et al.

[11] 4,039,669

[45] Aug. 2, 1977

[54] COMPOSITION FOR TOPICAL APPLICATION AND USE THEREOF

[75] Inventors: Arthur L. Beyler, North Greenbush; Richard A. Ferrari, Bethlehem, both of N.Y.

[73] Assignee: Sterling Drug Inc., New York, N.Y.

[21] Appl. No.: 601,192

[22] Filed: Aug. 1, 1975

[51] Int. Cl.² .............................................. A61K 31/56
[52] U.S. Cl. .................................. 424/243; 260/397.4
[58] Field of Search .......................... 260/397.4, 397.5; 424/239, 243

[56] References Cited

U.S. PATENT DOCUMENTS 2,855,341  10/1958  Meier et al. .......................... 424/239

FOREIGN PATENT DOCUMENTS 846,920  9/1960  United Kingdom .............. 260/397.4
854,407  11/1910  United Kingdom .............. 260/397.4

*Primary Examiner*—Elbert L. Roberts
*Attorney, Agent, or Firm*—Thomas L. Johnson; B. Woodrow Wyatt

[57] ABSTRACT

A composition for topical treatment of dermatological conditions associated with androgenic stimulatory influences, e.g. acne, which comprises 17α-R-androst-4-en-17β-ol-3-one or an ester thereof in an appropriate pharmaceutical formulation; and a method of treating such dermatological conditions therewith.

6 Claims, No Drawings

COMPOSITION FOR TOPICAL APPLICATION AND USE THEREOF

BACKGROUND OF THE INVENTION

1. Field of the Invention

This invention relates to a novel composition comprising a steroid having anti-androgenic activity and to a method for treating dermatological conditions therewith.

2. Description of the Prior Art

Certain dermatological conditions such as acne, seborrhea, hirsutism and male pattern baldness are directly associated with androgenic stimulatory influences. One possible method of ameliorating these conditions is to counteract the androgenic stimulatory influence by the use of a substance possessing anti-androgenic activity. The ideal anti-androgenic agent for the purpose here described is one which is active topically with no significant systemic side effects. An anti-androgenic with this profile has not heretofore been reported.

The progestin, cyproterone acetate (6-chloro-1α, 2α-methylene-4,6-pregnadien-17α-o1-3,20-dione acetate), is known as a systemic anti-androgen, but when tried topically it was reported not to be effective against acne or sebum secretion (Cunliffe et al. Brit. J. Dermat. 81:200, 1969).

Voigt and Hsia, *Endocrinology* 92:1216, 1973, have reported that 3-oxoandrost-4-ene-17β-carboxylic acid and the methyl ester thereof exhibit anti-androgenic activity in laboratory animals by virtue of inhibitory effects on steroid 5α-reductase activity; it did not, however, block the action of dihydrotestosterone on flank organ responses of castrated hamsters.

Methyltestosterone and 17α-ethylandrost-4-en-17β-ol -3-one, known lower homologs of 17α-(n-propyl) androst-4-en-17β-ol -3-one and 17α-(n-butyl) androst-4-en-17β-ol -3-one have systemic androgenic activity (Sauners, National Cancer Institute Monograph 12:139–159, 1963). The corresponding 19-nor-steroids, 17β-hydroxy-17-lower-alkylestr4-en-3-ones, are stated to be hypotensive and anabolic agents with low androgenic activity (Colton U.S. Pat. No. 2,721,871, issued Oct. 25, 1955).

17α-(n-Propyl) androst-4-en-17β-ol -3-one is known in the art only as an intermediate (Clinton U.S. Pat. No. 3,704,295, issued Nov. 28, 1972).

SUMMARY OF THE INVENTION

In a composition of matter aspect, the invention relates to a composition for topical treatment of dermatological conditions associated with androgenic stimulatory influences which comprises an anti-androgenically effective amount of 17α-R-androst-4-en-17β-ol3-one or a pharmaceutically acceptable ester thereof, where R is n-propyl or n-butyl, in a pharmaceutical formulation suitable for topical application.

In a further composition of matter aspect, the invention relates to 17α-(n-propyl)-17β-alkanoyloxyandrost-4-en-3-one where alkanoyl has from 1 to 10 carbon atoms.

In a still further composition of matter aspect, the invention relates to a compound selected from the group consisting of 17α-(n-butyl)androst-4-en-17β-ol3-one and alkanoic acid esters thereof wherein the ester moiety has from 1 to 10 carbon atoms.

In process aspect, the invention relates to a method of treating dermatological conditions associated with androgenic stimulatory influence which comprises applying to the affected skin area a composition comprising an anti-androgenically effective amount of 17α-R-anrost-4-en-17β-ol3-one or a pharmaceutically acceptable ester thereof, where R is n-propyl or n-butyl, in a pharmaceutical formulation suitable for topical application.

DETAILED DESCRIPTION INCLUSIVE OF PREFERRED EMBODIMENTS

It has been found that 17α-R-androst-4-en-17β-ol-3-ones of the formula

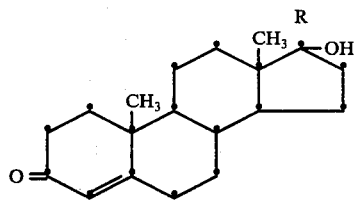

where R is $CH_2CH_2CH_3$ or $CH_2CH_2CH_2CH_3$ and pharmaceutically acceptable esters thereof are active as anti-androgenic agents upon topical application to mammalian organisms without manifesting any significant systemic effects. These compounds are therefore useful in preparations suitable for topical application for treatment of conditions associated with androgenic stimulatory influences, especially acne and seborrhea.

17α-R-Androst-4-en-17β-ol-3-one, where R is n-propyl or n-butyl, or a pharmaceutically acceptable ester thereof, exhibits the following properties which render it useful as a topical anti-androgenic agent.

1. It counteracts the actions of androgen when the latter is given topically or subcutaneously to castrated male hamsters or when the androgen is present normally in the intact male.

2. It impedes the actions of testosterone and dihydrotestosterone on sebaceous glands without modification of the response of the sex accessory organs to the androgen.

3. It is an effective inhibitor in vitro of the enzyme, steroid 5α-reductase, which catalyzes the conversion of testosterone to dihydrotestosterone, the latter being the alleged active androgen in sebaceous glands.

The effect of 17α-(n-propyl)androst-4-en-17β-ol-3-one and 17α-(n-butyl)androst-4-en-17β-ol-3-one on testosterone-stimulated flank organs and on endocrine organs in the castrated hamster was determined as follows:

Castrated hamsters were treated on both flank organs topically with testosterone propionate (TP) equivalent to 1 microgram of testosterone with or without the test agents dissolved in 5 microliters of absolute ethanol 14 times over a 2 weeks period. The hamsters were 4–5 weeks of age (55 to 75 grams body weight) and were caged individually. After the end of the two-weeks period, the development (degree of pigmentation) and diameter of the flank organs were assessed and measured, and the flank organs were punched out with an 8 mm cork borer for determination of wet weight and cholesterol content. Endocrine organ weights (adrenal gland, seminal vesicle and thymus gland) were also determined.

The results are given in the tables below. In the first table TP refers to testosterone propionate, Compd. I refers to 17α-(n-propyl)androst-4-en-17β-ol-3-one, Compd. II refers to 17α-(n-butyl)androst-4-en-17β-ol-3-one, and in refers to the number of animals in each group.

| Group | Treatment | (n) | Flank Organ, Mean ± S.E. Diameter (mm) | Wet Wgt (mg) | Cholest. (μg) | Flank Organ Develop. (Med. Score) |
|---|---|---|---|---|---|---|
| I | Vehicle Control | (8) | 2.21±0.16 | 36.7±0.95 | 79.6±2.9 | 0.0 |
| II | 1 μg TP | (8) | 4.30±0.15 | 42.0±1.2 | 238±26 | 4.0 |
| III | 1 μg TP + 100 μg Compd. I | (8) | 3.71±0.22 | 28.5±1.0 | 162±5.8 | 3.5 |
| IV | 1 μg TP + 200 μg Compd. I | (8) | 3.91±0.14 | 27.5±1.3 | 163±9.4 | 3.0 |
| V | 1 μg TP + 200 μg Compd. II | (7) | 3.24±0.13 | 21.6±1.2 | 151±8.9 | 1.0 |

| Group | Endocr. Organ Wgts (Mg), Mean ± S.E. Adrenal Gland | Seminal Vesicle | Thymus Gland |
|---|---|---|---|
| I | 11.4±.40 | 31.6±1.7 | 50.4±3.9 |
| II | 11.8±0.81 | 35.0±2.9 | 55.2±6.5 |
| III | 12.1±0.32 | 39.5±2.9 | 58.3±6.7 |
| IV | 11.6±0.48 | 34.0±2.6 | 43.5±4.9 |
| V | 12.4±0.53 | 34.0±4.1 | 60.7±7.6 |

The results of the foregoing tables show that both Compound I and Compound II were effective in reducing the testosterone-stimulated increase in flank organ diameter. Compound II was significantly more inhibitory than Compound I at the 200 μg dose level.

Both Compound I and Compound II reduced the wet weight of the flank organs below that recorded for the vehicle control. Compound II was more inhibitory than Compound I at the same dose level of 200 μg.

Both Compound I and Compound II were effective as inhibitors of the testosterone-stimulated increase in the cholesterol contact of the flank organs.

Both Compound I and Compound II were effective in suppressing flank organ development, as assessed by the degree of pigmentation evaluated by a median score ranging from a minimum of 0 to a maximum of 4. Compound II was substantially more effective than Compound I by this test, showing a median score of 1 as compared with 3 for Compound I at the same dose level of 200 μg.

The weights of the endocrine organs were not significantly altered by topical application of Compounds I or II.

Other test results on 17α-(n-propyl-4-en-17β-ol-3-one are as follows:

Daily application of 200 μg of 17α-(n-propyl)-androst-4-en-17β-ol-3-one to normal, sexually mature male hamsters caused a regression in flank organ development such that at 6 weeks the flank organ sebaceous glands resembled those found in immature hamsters. Size and lipid content of the sebaceous glands were significantly reduced; however, the seminal vesicle weights of the hamsters were not reduced.

The effectiveness of 17α-(n-propyl)androst-4-en-17β-ol-3-one in inhibiting the conversion of testosterone dihydrotestosterone by the enzyme steroid 5α-reductase was measured using minced hamster flank organ as a source of the enzyme and tritiated testosterone as a substrate. At concentrations of one-hundredth molar and one-thousandth molar, 17α-(n-propyl)androst-4-en-17β-ol-3-one was 100% and 53% inhibitory, respectively.

17α-(n-Propyl)androst-4-en-17β-ol-3-one in standard test procedures was found devoid of any significant androgenic, estrogenic or anabolic properties. In the Clauberg assay 32 mg/kg of 17α-(n-propyl)androst-4-en-17β-ol-3-one applied topically was found to have minimal progestational activity whereas 2 mg/kg of progesterone also applied topically gave a maximal response.

When 17α-(n-propyl)androst-4-en-17β-ol-3-one was administered intramuscularly, its progestational activity was about one-fortieth that of progesterone.

When 17α-(n-propyl)androst-4-en-17β-ol-3-one was topically applied to sexually mature hamsters at 200 μper flank organ for a period of 3 weeks, serum testosterone levels were unchanged compared with untreated controls.

The subcutaneous and oral toxicities (LD$_{50}$) for 17α-(n-propyl)androst-4-en-17β-ol-3-one were found to be >1000 mg/kg and >5000 mg/kg, respectively, in both the mouse and the rat. 17α-(n-Propyl)-androst-4-en-17β-ol-3-one is conveniently prepared by a three-step synthesis from 3β- acetoxyandrost-5-en-17-one in an over-all yield of 43%. The first step is a Grignard reaction with allylmagnesium bromide to give 17α-allylandrost-5-ene-3β,17β-diol in 81% yield. The second step is a hydrogenation over 10% palladium-on-carbon catalyst to afford 17α-propylandrost-5-ene-3β17β-diol in 88% yield. The third step is an Oppenauer oxidation with aluminum isopropoxide to give the desired 17α-(n-propyl)androst-4-en-17β-ol-3-one can be prepared by interacting androst-5-ene-3β-ol-17-one 3-tetrahydropyranyl ether with n-butyllithium, removing the tetrahydropyranyl group by acid hydrolysis to produce 17α-(n-butyl)androst-5-ene-3β,17β-diol and oxidizing the latter by the Oppenauer method using aluminum isopropoxide.

The therapeutically acceptable esters of 17α-(n-propyl)androst-4-en-17β-ol-3-one and 17α-(n-butyl)androst- 4-en-17β-ol-3-one are preferably those derived from carboxylic acids having from 1 to 12 carbon atoms and molecular weights less than about 250. Representative of the acyl moiety in said esters are alkanoyl, e.g. formyl, propionyl, butyryl, isobutyryl, caproyl, octanoyl, decanoyl, dodecanoyl, and the like; haloalkanoyl, e.g. chloroacetyl, trifluoroacetyl, and the like; carboxyalkanoyl, e.g. succinyl, glutaryl, and the like; cycloalkylalkanoyl, wherein cycloalkyl preferably has 5-6 ring members, e.g. β-cyclopentyl- propionyl, γ-cyclohexylbutyryl, and the like; benzoyl; phenylalkanoyl or -alkenoyl, e.g. phenylacetyl, β-phenylpropionyl, cinnamoyl, and the like; phenoxyalkanoyl, e.g. phenoxyacetyl, and the like; and aminoacyl, e.g. nicotinoyl, isonicotinoyl, dimethylaminopropionyl, γ-morpholinobutyryl, and the like. In acyl radicals containing a phenyl group, the latter can be unsubstituted or substituted by from one to three substituents, inert under the conditions used to make the esters, including lower-alkyl, lower-alkoxy, halogen, nitro and the like.

The esters of 17α-(n-propyl)androst-4-en-17β-ol-3-one or 17α-(n-butyl)androst-4-en-17β-ol-3-one are prepared from the parent alcohol by conventional esterificartion reactions as by interaction with the appropriate acid halide or acid anhydride.

EXAMPLE 1

17β-Formyloxy-17β-(n-propyl)androst-4-en-3-one a mixture of 20.4 ml. of acetic anhydride and 8.6 ml. of formic acid was warmed at 55°C. for 2 hours. To the resulting solution containing formic-acetic anhydride was added 5.00 g. of 17α-(n-propyl)androst-4-en-17β-ol-3-one, and the mixture was heated at 55°C. for 4 hours. The reaction mixture was then poured into ice water and extracted with methylene dichloride. The extracts were washed with sodium bicarbonate solution and water and the solvent removed. Thin layer chromatography indicated that some starting material was still present, so the crude product was heated for 4 hours at 55°C. with a fresh batch of formic-acetic anhydride prepared as described above. The solvent was removed by distillation at reduced pressure, and the residue taken up in 50 ml. of methylene dichloride, washed with sodium bicarbonate solution, filtered and concentrated. The residue was crystallized from an etherpentane mixture to give 2.54 g. of 17β-formyloxy-17α-(n-propyl)androst-4-en-3-one, m.p. 121°–122° C. when recrystallized from methanol; $[\alpha]_D^{25} = 53.4°$ (1% in chloroform).

The corresponding acetate, 17β-acetoxy-17α-(n-propyl)androst-4-en-3-one can be prepared by heating 17α-(n-propyl)androst-4-en-17β-ol-3-one with acetic anhydride in pyridine, or with acetic acid and acetic anhydride in the presence of p-toluenesulfonic acid.

Similarly, using the appropriate acid anhydride or acid halide there can be prepared the following esters:
17β-caproyloxy-17α-(n-propyl)androst-4-en-3-one,
17β-decanoyloxy-17α-(n-propyl)androst-4-en-3-one,
17β-trifluoroacetoxy-17α-(n-propyl)androst-4-en-3-one,
17β-succinyloxy-17α-(n-propyl)androst-4-en-3-one,
17β-glutaryloxy-17α-(n-propyl)androst-4-en-3-one,
17β-(β-cyclopentylpropionyloxy)-17α-(n-propyl)androst-4-en-3-one,
17β-(γ-cyclohexylbutyryloxy)-17α-(n-propyl)androst-4-en-3-one,
17β-benzoyloxy-17α-(n-propyl)androst-4-en-3-one,
17β-phenylacetoxy-17α-(n-propyl)androst-4-en-3-one,
17β-cinnamoyloxy-17α-(n-propyl)-androst-4-en-3-one,
17β-phenoxyacetoxy-17α-(n-propyl)-androst-4-en-3-one,
17β-nicotinoyloxy-17α-(n-propyl)androst-4-en-3-one,
17β-(γ-morpholinobutyryloxy)-17α-(n-propyl)androst-4-en-3-one,
17β-(p-chlorobenzoyloxy)-17α-(n-propyl)-androst-4-en-3-one,
17β-(3,4,5-trimethoxybenzoyloxy)-17α-(n-propyl)-androst-4-en-3-one,
17β-(m-nitrobenzoyloxy)-17α-(n-propyl)androst-4-en-3-one, and
17β-(p-chlorophenoxyacetoxy)-17α-(n-propyl)-androst-4-en-3-one.

Similarly, the corresponding esters of 17β-(n-butyl)androst-4-en-17-ol-3-one can be prepared.

17β-Formyloxy-17α-(n-propyl)androst-4-en-3-one when tested at 200 μ topically along with 1 μ of testosterone propionate on the flank organ of castrated hamsters, slightly reduced flank organ size, had no effect on flank organ development, reduced wet weight by about 13% and cholesterol content by 32%. By the last parameter, the formate ester was about 40% as active as the parent alcohol.

EXAMPLE 2 a. 17β-(n-Butyl)androst-5-ene-3β,17β-diol

To a solution of 101.6 g. of androst-5-ene-3β-ol-17-one 3-tetrahydropyranyl ether held under a nitrogen atmosphere was added 1 mole of butyllithium (2.4M in hexane, 417 ml.) and the mixture was stirred for about 16 hours at room temperature. An additional 0.25 mole of butyllithium (2.4M in hexane, 100 ml.) was then added, and the reaction mixture was heated at reflux for about 16 hours and allowed to stand at room temperature under nitrogen for 2 days. The solvent was removed by distillation and the residue partitioned between ether and ice-water containing ammonium chloride. The ether layer was separated and washed with water and the saturated sodium chloride solution, dried over anhydrous sodium sulfate and concentrated by distillation to an amber oil.

The resulting crude 3-tetrahydropyranyl ether of 17α-(n-butyl)androst-5-ene-3β,17β-diol was dissolved in 500 ml. of 95% ethanol containing 5.0 g. of p-toluenesulfonic acid, and the mixture was heated on a steam bath for 30 minutes. The acid was neutralized with 2.0 g. of potassium hydroxide, the solvent removed by distillation in vacuo, and the residue partitioned between ether and water. The ether solution was washed with saturated sodium chloride and dried over anhydrous sodium sulfate. Thin layer chromatography showed the product to be a mixture suggesting the presence of unreacted 17-oxo compound. Accordingly, there was added to the ether solution 51.0 g. of Girard's P reagent, 800 ml. of ethanol and 80 ml. of acetic acid, and this mixture was heated at reflux for 3 hours and then diluted to about 4500 ml. with water. The aqueous mixture was extracted 4 times with ether, and the ether extracts washed with sodium bicarbonate solution, water, and saturated sodium chloride solution, and dried over anhydrous sodium sulfate. The solvent was removed in vacuo, and the residue was dissolved in 1 liter of methylene dichloride and chromatographed on a column of 2 kg. of alumina pretreated with ether, ether containing increasing amounts of methylene dichloride, and finally with methylene dichloride alone. The column was eluted with methylene dichloride containing increasing amounts of ether until the ether content was 75%, then with 1 and 2% of methanol added. Eluant containing 2% methanol, 75% ether and 23% methylene dichloride brought out 34.4 g. of crystalline product which when recrystallized from ethyl acetate and then twice from methanol gave 13.4 g. of 17β-(n-butyl)androst-5-ene-3,17-diol, m.p. 144°–146° C.

b. 17α-(n-Butyl)androst-4-en-17β-ol-3-one

A solution of 13.4 g. of 17α-(n-butyl)androst-5-ene-3β,17β-diol and 52 ml. of 1-methyl-4-piperidone in 300 ml. of toluene was distilled to remove about 50 ml. of toluene and traces of moisture. To the resulting solution was added 19.5 g. of purified aluminum isopropoxide, and the mixture was heated with slow distillation for about one hour such that 125 ml. of distillate was collected. The reaction mixture was cooled in an ice bath, and excess 3N hydrochloric acid was added until the mixture was strongly acidic. The layers were separated and the aqueous layer extracted with benzene. The combined organic layers were washed with dilute hydrochloric acid and saturated sodium chloride solution, and dried over anhydrous magnesium sulfate. The solvent was removed and the residue crystallized and recrystallized from chloroform to give 6.0 g. of 17α-(n-butyl)androst-4-en-17β-ol-3one in the form of colorless prisms, m.p. 73°-74° C. (softening at 71°) containing solvent of crystallization. The latter was dried at 60° C. (0.1 mm.) for 8 hours to give 17α-(n-butyl)androst-4-en-17β-ol-3-one as a glass-like substance containing 0.55 mole of chloroform, $[\alpha]_D^{25}$ (1% in chloroform) = +54.6°.

The 17α-R-androst-4-en-17β-ol-3-one or a therapeutically acceptable ester thereof when prepared for use topically can be incorporated with various excipients to form solutions, suspensions, gels, ointments or creams. These excipients include, for example, such substances as water, ethanol, glycerol, carboxypolymethylene (Carbopol), ethylhydroxyethylcellulose, methylcellulose (Methocel), tyloxapol (Superinone), fire-dried fumed silica (Cab-O-Sil), complex magnesium-aluminum silicate gelling agent (Veegum), swelling clay, tris(hydroxymethyl)aminomethane, triethanolamine, and selected perfumes. The steroid is preferably present in a concentration of 0.1 to 5.0 percent by weight relative to the total weight of the formulations.

The following gel formulations containing 17α-(n-propyl)androst-4-en-17β-ol-3-one (Compd. I) were prepared:

|  | Formulations (% w/w) | | |
|---|---|---|---|
|  | 1 | 2 | 3 |
| Compd. I | 5.0 | 1.00 | 0.200 |
| Acetone | 16.0 | 16.0 | 16.0 |
| Ethanol (95% v/v) | 41.0 | 41.0 | 41.0 |
| Superinone | 1.00 | 1.00 | 1.00 |
| Carbopol 940 | 1.50 | 1.50 | 1.50 |
| Propylene glycol | 7.00 | 7.00 | 7.00 |
| Monoisopropanolamine | 0.125 | 0.125 | 0.125 |
| Purified water | 28.5 | 32.5 | 33.3 |
|  | 4 | 5 | 6 |
| Compd. I | 1.00 | 1.00 | 1.00 |
| Ethanol (95% v/v) | 41.0 | 41.0 | — |
| Superinone | 1.00 | 1.00 | — |
| Propylene glycol | 20.0 | 20.0 | — |
| Monoisopropanolamine | 0.120 | — | — |
| Carbopol 940 | 1.00 | — | — |
| Methocel 60HG, 4000 cps | — | 1.50 | — |
| Veegum PRO | — | — | 10.0 |
| Purified Water | 35.9 | 36.5 | 89.0 |

The foregoing formulations 1-5 can be prepared in the form of solutions of low viscosity ("splash" formulations) by omitting the Carbopol gelling agent.

We claim:

1. A composition for topical treatment of dermatological conditions associated with androgenic stimulatory influences which comprises an anti-androgenically effective amount of 17α-R-andros-4-en-17β-ol-3-one or a pharmaceutically acceptable ester thereof, where R is n-propyl or n-butyl, in a pharmaceutical formulation suitable for topical application.

2. A composition according to claim 1 in which the anti-androgenically effective compound is 17α-(n-propyl)androst-4-en-17β-ol-3one in a concentration of 0.1 to 5.0 percent by weight.

3. A composition according to claim 1 in which the anti-androgenically effective compound is 17α-(n-butyl)androst-4-en-17β-ol-3one in a concentration of 0.1 to 5.0 percent by weight.

4. A method of treating dermatological conditions associated with androgenic stimulatory influences which comprises applying to the affected skin area a composition according to claim 1.

5. A method of treating dermatological conditions associated with androgenic stimulatory influences which comprises applying to the affected skin area a composition according to claim 2.

6. A method of treating dermatological conditions associated with androgenic stimulatory influences which comprises applying to the affected skin area a composition according to claim 3.

UNITED STATES PATENT AND TRADEMARK OFFICE
CERTIFICATE OF CORRECTION

PATENT NO. : 4,039,669
DATED : August 2, 1977
INVENTOR(S) : Arthur L. Beyler and Richard A. Ferrari It is certified that error appears in the above-identified patent and that said Letters Patent are hereby corrected as shown below:

Cover page, second column, "11/1910" should read --11/1960--

Column 1, line 39, "Sauners" should read --Saunders--;
line 41, "-alkylestr4-" should read -- -alkylestr-4- --.

Column 2, line 4, "anrost" should read --androst--;
line 63, "Endoctrine" should read --Endocrine--.

Column 3, line 2, "and in" should read --and n--;
line 52, "17α-(n-propyl-4-en-17β-ol-3-one" should read
--17α-(n-propyl)androst-4-en-17β-ol-3-one--.

Column 4, line 32, "µper" should read --µg per--;
line 48, delete line in entirety and insert in place thereof:
--propyl)androst-4-en-17β-ol-3-one in 60.5% yield.
17α-(n-Butyl)androst-4-en-17β-ol-3-one can be prepared by--.

Column 5, line 16, "17β-(n-" should read --17α-(n- --;
line 34, "etherpentane" should read --ether-pentane--;
line 37, "53.4°" should read --+53.4°--.

Column 3, line 40, "contact" should read --content--;
line 64, insert --to-- before "dihydrotestosterone".

Column 8, line 17, opposite "Purified Water" and under Formulation 5, the figure "36.5" should read --35.5--.

UNITED STATES PATENT AND TRADEMARK OFFICE
CERTIFICATE OF CORRECTION

PATENT NO. : 4,039,669
DATED : August 2, 1977
INVENTOR(S) : Arthur L. Beyler and Richard A. Ferrari It is certified that error appears in the above-identified patent and that said Letters Patent are hereby corrected as shown below:

Column 6, line 5, "17β-(n-" should read --17α-(n- --;
line 8, "μ" should read --μg-- (both occurrences);
line 18, "17β-(n-" should read --17α-(n- --;
line 23, "0.25 mole" should read --0.24 mole--;
line 67, "17β-(n-" should read --17α-(n- --.

Column 8, line 26, Claim 1, "andros" should read --androst--; line 32, Claim 2, "3one" should read --3-one--; line 36, Claim 3, "3one" should read --3-one--.

Signed and Sealed this

Twenty-eighth Day of February 1978

[SEAL]

Attest:

RUTH C. MASON
Attesting Officer

LUTRELLE F. PARKER
Acting Commissioner of Patents and Trademarks